United States Patent [19]

Cosyns et al.

[11] Patent Number: 4,587,369

[45] Date of Patent: May 6, 1986

[54] SELECTIVELY HYDROGENATING ACETYLENIC COMPOUNDS IN A HIGH BUTADIENE CONTENT $C_4$ CUT

[75] Inventors: Jean Cosyns, Maule; Jean-Paul Boitiaux, Poissy, both of France

[73] Assignee: Institut Francais du Petrole, Rueil-Malmaison, France

[21] Appl. No.: 664,654

[22] Filed: Oct. 25, 1984

[30] Foreign Application Priority Data

Oct. 25, 1983 [FR] France ................... 83 16943

[51] Int. Cl.⁴ .................................... C07C 5/08
[52] U.S. Cl. ....................... 585/259; 208/143; 208/255; 585/260; 585/261
[58] Field of Search ........... 585/259, 260, 261; 208/143, 255

[56] References Cited

U.S. PATENT DOCUMENTS

| | | | |
|---|---|---|---|
| 2,913,405 | 11/1959 | Shalit | 208/255 |
| 2,970,177 | 1/1961 | Cobb, Jr. | 585/259 |
| 3,051,647 | 8/1962 | White | 208/255 |
| 3,316,318 | 4/1967 | Voetter et al. | 385/259 |
| 3,654,129 | 4/1972 | Bloch | 208/255 |
| 3,654,132 | 4/1972 | Christman et al. | 208/143 |
| 3,670,041 | 6/1972 | Juki et al. | 208/255 |
| 3,770,619 | 11/1973 | Deurlen et al. | 208/255 |
| 4,216,078 | 8/1980 | Plumlee et al. | 208/143 |
| 4,447,556 | 5/1984 | O'Hara et al. | 208/143 |

FOREIGN PATENT DOCUMENTS

| | | | |
|---|---|---|---|
| 865299 | 4/1961 | United Kingdom | 585/259 |
| 1361940 | 7/1974 | United Kingdom | 585/259 |

*Primary Examiner*—William R. Dixon, Jr.
*Assistant Examiner*—Cynthia A. Prezlock
*Attorney, Agent, or Firm*—Millen & White

[57] ABSTRACT

A $C_4$ cut of high butadiene content is selectively hydrogenated in contact with a supported palladium catalyst, the operation being performed in admixture with a hydrocarbon and an amine.

The $C_4$ cut of high butadiene content (1) and liquid hydrocarbon containing the amine (6) pass through reactor (2). The resultant product is fractionated (13). The $C_4$ cut is recovered in the vapor phase (15) and the liquid phase recycled (16).

16 Claims, 1 Drawing Figure

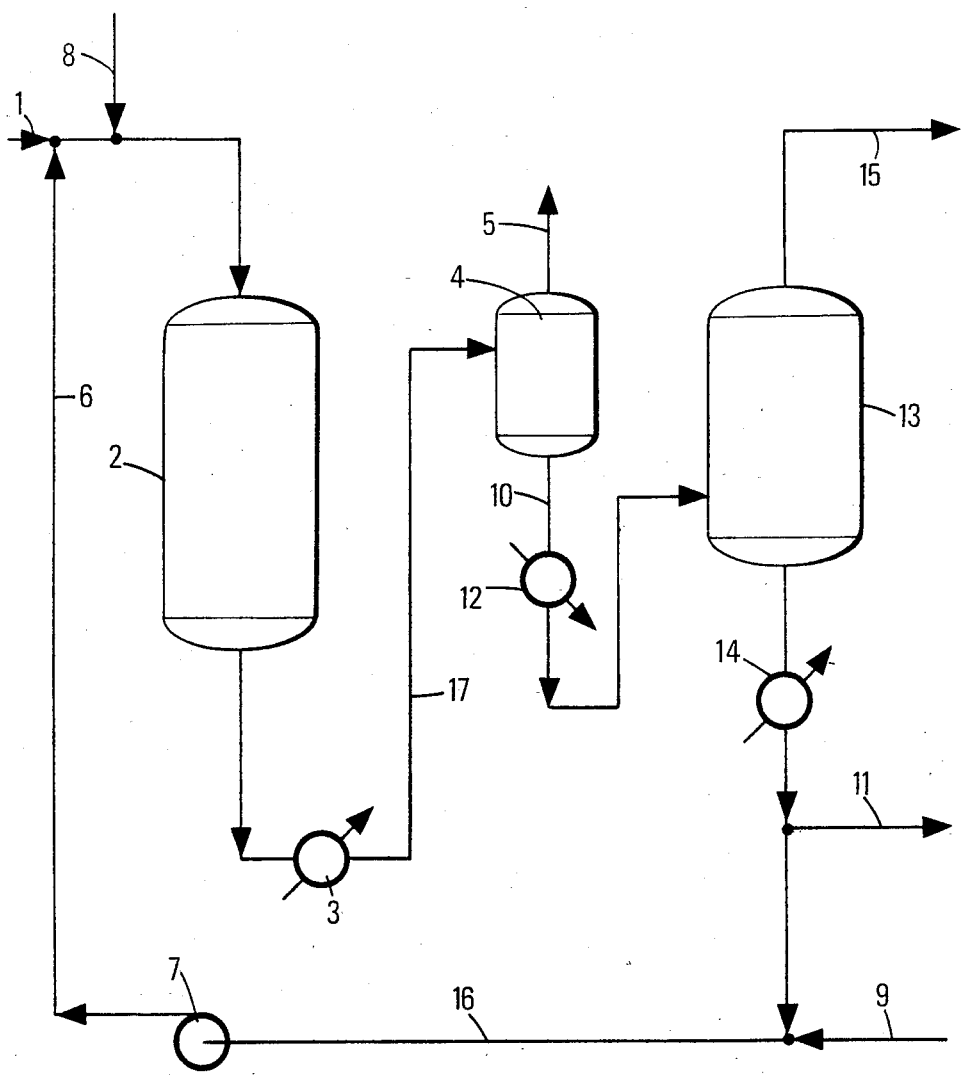

SELECTIVELY HYDROGENATING ACETYLENIC COMPOUNDS IN A HIGH BUTADIENE CONTENT C4 CUT

BACKGROUND OF THE INVENTION

High-temperature conversion processes as steam-cracking provide a wide range of unsaturated hydrocarbons, normally in gaseous state such as ethylene, propylene, butadiene and butenes, and in liquid state such as $C_5$, $C_6$, $C_7$ olefins forming part of pyrolysis gasoline.

These products can be separated by mere fractionation, depending on their distillation range, thus providing $C_2$, $C_3$, $C_4$ cuts and gasoline.

However, each of these cuts is a mixture of paraffinic, monoolefinic, diolefinic and acetylenic hydrocarbons.

For example, a typical composition of $C_4$ cut is as follows:

| | |
|---|---|
| Butadiene | 20–50% by weight |
| Butane | 10–20% " |
| Butenes | 20–50% " |
| Butynes | 0.05–0.2% " |
| Vinylacetylene | 1–3% " |

It may happen that the $C_4$ cut contains a minor proportion of $C_3$ or $C_5$ hydrocarbons, for example up to 5% by weight.

Upgrading of butadiene contained in said cut is only achievable after removal of butyne and vinylacetylene.

This purification may be performed by: extractive distillation or/and selective hydrogenation.

Extractive distillation provides butadiene containing less than 100 ppm by weight of vinylacetylene but this limit is only achieved at the cost of a significant butadiene loss. As a matter of fact, fractionation of said cut purifies butadiene by increasing the concentration of acetylenics in a secondary effluent which, generally, is burnt.

The explosiveness of high concentrations of components in said secondary effluent requires dilution with products which could otherwise be upgraded such as butadiene and butenes, thus decreasing substantially the yield of the plant.

For this reason, a selective hydrogenation unit is generally provided, upstream of the extraction unit, which decreases the acetylenic content of the mixture to be separated, thus proportionally decreasing the butadiene losses due to dilution.

However, this improvement in butadiene yield is only substantial when hydrogenation is really selective.

This hydrogenation is generally performed in liquid phase at temperature of 10°–80° C., under pressures of 4–10 bars, over a palladium-containing catalyst.

The known processes now used result in such ion butadiene yields that the overall saving achieved by this additional hydrogenation step is marginal.

OBJECT OF THE INVENTION

The object of the invention is to provide a new catalytic process for selective hydrogenation in the liquid phase, which can be operated under mild conditions and whereby the activity and selectivity of the catalyst are improved.

SUMMARY OF THE INVENTION

The process of the invention consists of selectively hydrogenating a $C_4$ cut in presence of a palladium-on-alumina catalyst in a diluent which is a liquid phase comprising at least one aromatic hydrocarbon and one amine compound in solution. The presence of amine surprisingly improves the activity and the selectivity of the catalyst; this promoting effect, already substantial with paraffinic solvents, is even more enhanced with aromatic solvents. The liquid phase or diluent contains 5 to 100% by weight of at least one aromatic hydrocarbon.

The hydrocarbon (or hydrocarbons) of the liquid phase or diluent is (are) substantially inert during the hydrogenation. At least one aromatic hydrocarbon is used, either alone or as a mixture with one or more saturated, paraffinic or cyclic, hydrocarbons. Monoolefinic hydrocarbons may also be used in view of the high selectivity of the reaction. Examples of non aromatic hydrocarbons are heptane, dodecane, isooctane, cyclohexane, tetrahydronaphthalene, a naphtha cut or a kerosene cut. Examples of aromatic hydrocarbons are benzene, toluene, ethylbenzene.

Preferably the one or more hydrocarbons of the liquid phase is (are) so selected that it (they) can be easily separated from the hydrogenation products; preferably the hydrocarbon (s) will have a boiling point substantially higher than that of the treated cut, for example by at least 10° C. and preferably at least 50° C.

The proportion of amine compound is for example 0.01 to 10%, preferably 0.1 to 2% of the total weight of the liquid phase of $C_4$ cut+diluent. The amine compound is an amine or a polyamine. The amine is preferably a primary or secondary, aliphatic or cyclic amine; it may also be a tertiary amine.

The amine may comprise substituents or groups other than the amine group which do not impede the reaction, for example alcohol or ether groups. Examples of amine compounds are: methylamine, ethylamine, diethylamine, trimethylamine, piperidine, morpholine, piperazine, ethylenediamine, diethylenetriamine, 1,3-propanolamine, ethanolamine, diethanolamine, bis(amino-ethyl)ether, aniline, butylamine.

Amines of heterocyclic structure (of the quinoline or pyridine type) form no part of the invention.

The hydrogenation catalyst consists of supported palladium. Palladium is generally deposited in a proportion of 0.01 to 1% by weight on an alumina carrier. Alumina has preferably a surface from 5 to 100 m2/q. One or more other metals, such as silver or gold for example, may be associated to palladium. Their proportions may range for example from 0.01 to 1% by weight of the catalyst. Preferably the ratio by weight Au/Pd or Ag/Pd is lower than 1. Gold gives particularly interesting results, the ratio by weight Au/Pd being preferably from 0.05 to 0.5.

The hydrogenation is performed in a reactor fixed bed catalytic.

BRIEF DESCRIPTION OF THE DRAWING

The accompanying drawing is a flow-sheet illustrating an example of embodiment of the invention.

A more detailed description of the invention is given hereinafter with reference to said an embodiment.

The cut to be hydrogenated (1), hydrogen (8) and liquid diluent (6) are introduced into reactor (2).

After cooling in exchanger (3), the liquid-gas mixture is introduced through line (17) into the flash drum (4) wherein hydrogen gas excess (5) is separated from the diluent and liquid hydrogenated cut (10). The liquid phase is partially vaporized in exchanger (12) and introduced into the flash drum (13) wherein the gaseous purified cut is separated from the liquid diluent. The purified cut is fed, through line (15), to the butadiene extraction unit. The liquid diluent, after cooling in exchanger (14), is recycled through line (16) and pump (7). Line (11) is provided for purging a part of the solvent and line (9) for introducing additional fresh solvent.

The hydrogenation operating conditions are as follows:

Space velocity expressed as volumetric flow rate of liquid hydrocarbon cut per volume of catalyst per hour (VVH liq): 0.5–30, preferably 1–10.

Total pressure: 5–50 bars

Temperature: 20°–150° C.

Ratio of hydrogen to acetylenics, expressed in moles per mole: 1–10, preferably 1–2

Solvent (diluent + amine compound) flow rate advantageously adjusted to 5–50%, preferably 10–30% by weight of the feed rate of the cut to be hydrogenated Amine content adjusted to 0.01–10% by weight of the total hydrocarbons (inert hydrocarbons (diluent) + $C_4$ cut) and preferably to 0.1–2% of this weight.

EXAMPLES

The following non limitative examples illustrate the invention.

EXAMPLE 1

This example illustrates a prior art technique for hydrogenating a diolefinic $C_4$ cut having the following composition by weight:

Butadiene: 46%
Butane: 11%
Butenes: 41.55%
Vinylacetylene: 1.45%

The catalyst contains 0.2% palladium on an alumina carrier having a specific surface of 70 m2/g and a pore volume of 0.6 cc/g. The catalyst is arranged as a fixed bed in a tubular reactor; the liquid $C_4$ cut is passed through the reactor under the following conditions:

$VVH_{liq}$: 8
Pressure: 5 bars
Temperature: 25° C.
$H_2$/VAC: 1–2 moles/mole

The hydrogen/vinylacetylene ratio is so adjusted that the hydrogenated cut contains respectively 1000 or 100 ppm of residual vinylacetylene.

Table 1 reports the results; butadiene yields are given for each value of vinylacetylene conversion. These yields are expressed as the proportion of butadiene content of the hydrogenated cut to butadiene content of the cut to be hydrogenated.

TABLE 1

| Residual vinylacetylene content (ppm) | 1000 | 100 |
|---|---|---|
| Butadiene yield (%) | 98.35 | 97.32 |

EXAMPLE 2

The same $C_4$ cut as in example 1 is hydrogenated, but with addition of 10% by weight of n-heptane and of an amount of amine compound, expressed in proportion of the total liquid feed, $C_4$ cut + n-heptane, of 1.3% by weight.

After hydrogenation, the effluent is partially vaporized so that the $C_4$ cut separates from the mixture n-heptane + amine, this mixture of being recycled as shown in the flow-sheet of the figure.

The operating conditions are the same as in example 1. Table 2 reports the results in three cases: addition of 10% n-heptane, addition of 10% n-heptane + 1.3% piperidine, and addition of 10% n-heptane + 1.3% butylamine. The results are expressed as butadiene yield, as in example 1.

TABLE 2

| Residual vinylacetylene content (ppm) | 1000 | 100 |
|---|---|---|
| n-heptane | 98.95 | 97.83 |
| n-heptane + piperidine | 99.50 | 98.40 |
| n-heptane + butylamine | 99.65 | 98.50 |

It is apparent that the addition of amine to the reaction medium provides for a substantial increase of butadiene yields.

EXAMPLE 3

In this example according to the invention, the same $C_4$ cut as in example 1 is hydrogenated but with addition to the cut of 10% by weight of toluene and 1.3% by weight of amine compound, said latter proportion being expressed with respect to the total liquid feed rate of $C_4$ cut + toluene.

The operating conditions are the same as in example 1 and table 3 reports the results in three cases: Addition of 10% toluene, addition of 10% toluene + 1.3 piperidine, and addition of 10% toluene + 1.3% butylamine.

The results are expressed as butadiene yield, as in example 1.

TABLE 3

| Residual vinylacetylene content (ppm) | 1000 | 100 |
|---|---|---|
| Toluene | 99.1 | 98.2 |
| Toluene + piperidine | 99.96 | 99.2 |
| Toluene + butylamine | 99.92 | 98.9 |

It is apparent that the addition of amine to an aromatic solvent is more favorable than to a paraffinic solvent.

EXAMPLE 4

In this example, hydrogenation is conducted under the same conditions as in the preceding example, but with the use as solvent of a 50–50 by weight mixture of n-heptane and toluene. Results are reported in table 4 (giving the butadiene yield).

TABLE 4

| Residual vinylacetylene content (ppm) | 1000 | 100 |
|---|---|---|
| Toluene + heptane | 99.4 | 98.6 |
| Toluene + heptane + piperidine | 99.9 | 99.0 |

EXAMPLE 5

In this example, hydrogenation is conducted under the same conditions as in example 3 but with addition of amine compound in under proportion of an 0.1% of the total liquid feed, $C_4$ cut + toluene. The amine compounds are piperidine and butylamine. Results are reported in table 5, giving the butadiene yield.

TABLE 5

| Residual vinylacetylene content (ppm) | 1000 | 100 |
|---|---|---|
| Toluene + piperidine | 99.94 | 99.15 |
| Toluene + butylamine | 99.85 | 98.7 |

EXAMPLE 6 (not conforming with the invention)

In this example, hydrogenation is conducted under the same conditions as in example 3 but with the addition of a nitrogenous compound in a proportion of 1.3% of the total weight of liquid feed, $C_4$ cut + toluene. Here, the nitrogenous compounds are pyridine and quinoline. Results are reported in table 6, giving the butadiene yield.

TABLE 6

| Vinylacetylene content (ppm) | 1000 | 100 |
|---|---|---|
| Toluene + pyridine | 99.1 | 98.2 |
| Toluene + quinoline | 99.3 | 98.3 |

EXAMPLE 7

In this example, hydrogenation is performed in the same conditions as in under example 5, using piperidine but with a catalyst containing 0.2% palladium and 0.1% gold deposited on an alumina carrier having a specific surface of 70 m2/g and a pore volume of 0.6 cc/g. Piperidine is added to the $C_4$ cut to be hydrogenated, in a proportion of 0.1% by weight of the total liquid feed, $C_4$ cut + toluene. Results are reported in table 7.

TABLE 7

| Residual vinylacetylene content (ppm) | 1000 | 100 |
|---|---|---|
| Butadiene yields with use of toluene + piperidine | 99.96 | 99.3 |

What is claimed as the invention is:

1. In a process for selectively hydrogenating a $C_4$ hydrocarbon cut containing butadiene and at least one acetylenic hydrocarbon of the group comprising butynes and vinylacetylenes, wherein said cut, in the liquid phase, is contacted with a palladium catalyst deposited on alumina, and said $C_4$ cut is treated with hydrogen to selectively hydrogenate said acetylenic compounds, the improvement comprising conducting said hydrogenating of said $C_4$ cut in admixture with at least one aromatic hydrocarbon and at least one amine compound, said aromatic hydrocarbon being substantially inert during the hydrogenation and separable, at a later stage, from the reaction product, said amine compound being a primary or secondary amine.

2. A process according to claim 1, wherein the amine compound is a primary amine.

3. A process according to claim 1, wherein the amine compound is present in an amount of 0.01–10% by weight of the total hydrocarbons.

4. A process according to claim 3, wherein the amine compound is present in an amount of 0.01–2% by weight of the total hydrocarbons.

5. A process according to claim 1, wherein the proportion of substantially inert hydrocarbon and amine compound is 5–50% by weight of the $C_4$ cut.

6. A process according to claim 1, wherein the amine compound is selected from the group consisting of methylamie, ethylamine, diethylamine, piperidine, morpholine, piperazine, ethylene diamine, diethylenetriamine, 1,3-propanolamine, ethanolamine, diethanolamine, bis(aminoethyl)ether, aniline, and butylamine.

7. A process according to claim 1, wherein the catalyst comprises 0.01 to 1% by weight of palladium on alumina of 5–100 m2/g surface.

8. A process according to claim 1, wherein the catalyst further contains 0.01–1% by weight of gold.

9. A process according to claim 1, comprising the following operating conditions:
   volume tire flow rate of $C_4$ cut per volume of catalyst and per hour: 0.5–30;
   Temperature: 20°–150° C.;
   Total pressure: 5–50 bars;
   Molar ratio of hydrogen to acetylenic hydrocarbons: 1–10.

10. A process according to claim 9, characterized in that the volume flow rate is 1–10 and the molar ratio of hydrogen to acetylenic hydrocarbons 1–2.

11. A process according to claim 1 wherein said aromatic solvent is toluene.

12. A process according to claim 1 wherein the amine is piperidine or butylamine.

13. A process according to claim 11 wherein the amine is piperidine or butylamine.

14. A process according to claim 4 wherein the amine is piperidine or butylamine.

15. A process according to claim 7 wherein the amine is piperidine or butylamine.

16. A process according to claim 1 wherein the amine is non-aromatic.

* * * * *